United States Patent [19]
Vacanti

[11] Patent Number: 5,944,754
[45] Date of Patent: Aug. 31, 1999

[54] TISSUE RE-SURFACING WITH HYDROGEL-CELL COMPOSITIONS

[75] Inventor: Charles A. Vacanti, Lexington, Mass.

[73] Assignee: University of Massachusetts, Boston, Mass.

[21] Appl. No.: 08/747,036

[22] Filed: Nov. 8, 1996

Related U.S. Application Data

[60] Provisional application No. 60/006,426, Nov. 9, 1995.

[51] Int. Cl.[6] .............................. A61F 2/02; A61F 2/08; A61F 2/04; A61F 2/10; A61F 13/00; A61M 1/00
[52] U.S. Cl. .............................. 623/11; 623/12; 623/13; 623/15; 623/16; 602/48; 602/49; 604/28; 604/290
[58] Field of Search ................... 623/1, 11, 16, 623/12, 9, 13–15; 602/41–43, 45, 46, 48, 49, 50; 604/28, 290

[56] References Cited

U.S. PATENT DOCUMENTS

| | | | |
|---|---|---|---|
| 4,191,747 | 3/1980 | Scheicher | 424/94 |
| 4,846,835 | 7/1989 | Grande | 623/11 |
| 4,997,443 | 3/1991 | Walthall et al. | 623/11 |
| 5,041,138 | 8/1991 | Vacanti | 623/16 |
| 5,071,644 | 12/1991 | Viegas et al. | 514/772.7 |
| 5,126,141 | 6/1992 | Henry | 424/423 |
| 5,192,326 | 3/1993 | Bao et al. | 623/17 |
| 5,277,911 | 1/1994 | Viegas et al. | 424/427 |
| 5,292,516 | 3/1994 | Viegas et al. | 424/423 |
| 5,294,446 | 3/1994 | Schlameus et al. | 424/489 |
| 5,298,260 | 3/1994 | Viegas et al. | 424/486 |
| 5,300,295 | 4/1994 | Viegas et al. | 424/427 |
| 5,306,501 | 4/1994 | Viegas et al. | 424/423 |
| 5,318,780 | 6/1994 | Viegas et al. | 424/427 |
| 5,405,366 | 4/1995 | Fox et al. | 607/50 |
| 5,410,016 | 4/1995 | Hubbell et al. | 528/354 |
| 5,575,815 | 11/1996 | Slepian et al. | 623/11 |
| 5,593,974 | 1/1997 | Rosenberg et al. | 514/44 |

FOREIGN PATENT DOCUMENTS

| | | |
|---|---|---|
| 0 361 957 | 4/1990 | European Pat. Off. . |
| WO 92/06702 | 4/1992 | WIPO . |
| WO 93/16687 | 9/1993 | WIPO . |

*Primary Examiner*—David J. Isabella
*Assistant Examiner*—John M. Black
*Attorney, Agent, or Firm*—Fish & Richardson P.C.

[57] ABSTRACT

The invention provides compositions and methods for generating new tissue on a surface, e.g., a surface of damaged or lost tissue, of a structure or organ in a mammal, The methods involve applying a thin layer of a liquid hydrogel-cell composition to the surface; and allowing the liquid hydrogel-cell composition to solidify, thereby forming a matrix that enables the tissue precursor cells to grow and generate new tissue. The surface can be internal, e.g., the surface of an organ or the internal surface of a blood vessel, or external, e.g., skin.

17 Claims, No Drawings

5,944,754

TISSUE RE-SURFACING WITH HYDROGEL-CELL COMPOSITIONS

CROSS REFERENCE TO RELATED APPLICATIONS

This application claims benefit from U.S. Provisional Application Ser. No. 60/006,426, filed Nov. 9, 1995.

BACKGROUND OF THE INVENTION

The invention relates to methods of generating tissue on surfaces of animal organs and structures such as cartilage, bone, skin, and epithelial layers using a hydrogel-cell composition, to repair surfaces of tissue damaged by disease or injury.

Cartilage and Tissue Replacement

One of the primary needs for replacement cartilage is to correct defects in the articular surface of various joints. In recent years, several approaches have been attempted to generate cartilage and other tissues by entrapping or attaching cells to various synthetic and naturally occurring materials. Chondrocytes, for example, (1) have been delivered in gelatin, collagen, and the naturally occurring polymer alginate; (2) have been delivered attached to synthetic biodegradable polymers such as polyglycolic acid; and (3) have been immersed in fibrin and various hydrogels for delivery. Three-dimensional chondrocyte masses have been created using the above methods. In addition, polyglycolic acid has been applied as a cover for bone, but is fixed in place by suturing to the underlying bone.

Hydrogels

Polymerizable and biocompatible, and typically biodegradable, hydrogels have been used to deliver various compositions to different sites of implantation and for tissue support. For example, U.S. Pat. No. 5,071,644 describes the use of a thermo-irreversible gel for topical drug delivery to the skin of a mammal. The gels are described as aqueous mixtures of a polyoxyalkylene polymer and an ionic polysaccharide, optionally containing a latent counter-ion to gel the polysaccharide upon release of the counter-ion and to render the gelled mixture irreversible upon cooling.

Further, U.S. Pat. No. 5,298,260 describes a thermo-reversible gel suitable for medical devices or vehicles for drug delivery to the skin of a mammal. Additionally, U.S. Pat. No. 5,126,141 describes the use of thermo-irreversible gels of polyoxyalkylene polymers and ionic polysaccharides to reduce adhesion after surgery.

U.S. Pat. No. 5,318,780, describes the use of gels to deliver drugs or diagnostic agents to the eye, or body cavities, e.g., topically or by injection; as protective corneal shields; or as ablatable corneal masks useful in laser reprofiling of the cornea. Similarly, U.S. Pat. No. 5,300,295 describes aqueous gel drug delivery compositions and medical devices, useful for treating an eye condition, having hyperosmotic, iso-osmotic, or hypo-osmotic characteristics in the gel state.

U.S. Pat. No. 5,041,138 describes a method of surgically implanting a polymeric matrix containing cells to form a cartilaginous structure. The matrix is shaped prior to implantation to form a desired anatomical structure.

U.S. Pat. No. 5,410,016 describes hydrogels of polymerized and cross-linked macromers. These hydrogels are used to prevent adhesion of tissues after surgical procedures, for the controlled release of drugs and other bioactive materials, to temporarily protect tissue surfaces, to adhere or seal tissues together, and to prevent the attachment of cells to tissue surfaces. Also described is a modified water soluble gel system for encapsulating biological materials to be used as tissue adhesives, coatings for tissue lumens, and as drug delivery devices for biologically active materials (Hubbell, WO 93/16687, 1993).

SUMMARY OF THE INVENTION

The invention is based on the discovery that tissues can be re-surfaced with thin layers of hydrogel-cell compositions that contain living tissue precursor cells such as chondrocytes, osteoblasts, or epithelial cells. The hydrogel-cell compositions are easily applied, e.g., as a "paint," to a desired surface of, e.g., cartilage, a bone, skin, or an organ, and provide a thin matrix or scaffold within which the tissue precursor cells can adhere to the surface and grow, thereby generating a new thin surface tissue layer. The resulting newly generated tissue is similar in composition and histology to its naturally occurring counterpart tissue.

The hydrogel-cell compositions are created by suspending tissue precursor cells, preferably autologous cells, in various hydrogel systems. A thin layer of this hydrogel-cell composition is then applied to a circumscribed surface, e.g., a defect, enabling the tissue precursor cells to permanently adhere to the surface and to grow, thus forming a new tissue surface as the hydrogel erodes/degrades. This novel method for generating new tissue on an irregularly shaped surface involves painting, dripping, or spraying a hydrogel-cell composition directly onto the irregularly shaped surface. As a result of its inherent properties, the hydrogel quickly solidifies on the surface and eventually degrades, thereby leaving the living cells behind to form the desired new tissue which results in generation of a thin layer of new tissue, e.g., cartilage.

The methods of the invention can be used to generate new tissue growth on a variety of different mammalian surfaces such as skin, joints, pleural cavities, tracheal region, thoracic cavity, gastrointestinal tract, genito-urinary tract, scalp, bladder, stomach, nerve sheathes, cornea, oral cavity, nasal sinuses, bone, vessels of the cardiovascular system, esophagus, and vaginal wall. The claimed method therefore can be used on a variety of different mammalian tissue surfaces.

Tissue precursor cells can be epidermal cells; chondrocytes and other cells that form cartilage; dermal cells; muscle cells; hair follicles; fibroblasts; organ cells; macrophages; hepatocytes; osteoblasts and other cells that form bone; endothelial cells; mucosal cells, e.g., nasal, gastric, bladder and oral mucosal cells; pleural cells; ear canal cells; tympanic membrane cells; peritoneal cells; Schwann cells; corneal epithelial cells; gingiva cells; muscle cells; and tracheal epithelial cells.

In general, the invention features a method for generating new tissue on a surface of a structure or organ in a mammal by a) obtaining a liquid hydrogel-cell composition, e.g., by mixing a hydrogel with tissue precursor cells; b) applying a thin layer of the liquid hydrogel-cell composition to the surface; and c) allowing the liquid hydrogel-cell composition to solidify, thereby forming a matrix that enables the tissue precursor cells to grow and generate new tissue.

In particular embodiments, the hydrogel-cell composition is solidified or set upon exposure to the body temperature of the mammal, or by interaction with ions, e.g., copper, calcium, aluminum, magnesium, strontium, barium, tin, and di-, tri- or tetra-functional organic cations, low molecular weight dicarboxylate ions, sulfate ions, and carbonate ions. The hydrogel-cell composition can also be solidified upon exposure to radiation, e.g., ultraviolet or visible light. The hydrogel-cell composition can be further stabilized by cross-linking with a polyion.

In one embodiment, the method further includes the use of a biocompatible amount of an adhesive, e.g., methyl alpha-cyanoacrylate, methacrylate, 2-cyano-2-propenoic acid methyl ester, methyl 2-cyanoacrylate, 2-cyanoacrylic acid methyl ester, and n-butyl cyanoacrylate based glue.

In a particular embodiment, the invention features a method for generating new cartilage to replace a damaged cartilage surface on a bone in a mammal, by obtaining a liquid hydrogel-chondrocyte composition; applying a thin layer of the liquid hydrogel-chondrocyte composition to the damaged cartilage surface in the mammal; and allowing the liquid hydrogel-chondrocyte composition to solidify, thereby forming a matrix that enables the chondrocytes to grow and generate new cartilage.

In another example, the hydrogel-cell composition can be applied to damaged tissue surfaces of skin, e.g., in two layers with a first hydrogel-cell layer including dermal cells and a second hydrogel-cell layer including epidermal cells. In addition, the hydrogel-cell composition can include epithelial cells and be applied to damaged tissue surfaces of the inner lumen walls of blood vessels.

In another aspect, the invention features a hydrogel-cell composition including a temperature-sensitive hydrogel and isolated human chondrocytes at a concentration of from 10 to 50 million cells per ml of hydrogel. The invention also features a system for repairing a bone defect, the system including a plug made of, e.g., porous hydroxyapatite, and a hydrogel-chondrocyte, e.g., autologous chondrocyte, composition. The plug is dimensioned to fit within the bone defect, and the hydrogel-chondrocyte composition is applied to the surface of the plug after the plug is inserted into the defect.

As used herein, a "hydrogel" is defined as a substance formed when an organic polymer (natural or synthetic) is set or solidified to create a three-dimensional open-lattice structure that entraps water, or other solution, molecules to form a gel. The solidification can occur, e.g., by aggregation, coagulation, hydrophobic interactions, or cross-linking. The hydrogels employed in this invention rapidly solidify to keep the cells at the application site thereby eliminating problems of phagocytosis or cellular death and enhancing new cell growth at the application site. The hydrogels used in this invention are also biocompatible, e.g., not toxic, to cells suspended in the hydrogel.

As used herein, a "hydrogel-cell composition" is a suspension of a hydrogel containing desired tissue precursor cells. These cells can be isolated directly from a tissue source or can be obtained from a cell culture. For this invention, a "tissue" is a collection or aggregation of particular cells embedded within its natural matrix, wherein the natural matrix is produced by the particular living cells. "Tissue precursor cells" are cells that form the basis of new tissue.

As used herein, "organ cells" include hepatocytes, islet cells, cells of intestinal origin, cells derived from the kidney, and other cells acting primarily to synthesize and secret, or to metabolize materials.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, useful methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

The invention provides methods for applying thin layers of hydrogel-cell compositions containing living tissue precursor cells capable of cell division to promote new functional and structural tissue generation at the application site.

Hydrogels

The hydrogels used to practice this invention should be biocompatible and biodegradable, should solidify rapidly in vivo, i.e., in about 5 minutes or less after application, and should be capable of sustaining living cells during the time period between application and solidification.

Examples of different hydrogels suitable for practicing this invention, include, but are not limited to: (1) temperature dependent hydrogel that solidify or set at body temperature, e.g., PLURONICS™; (2) hydrogels cross-linked by ions, e.g., sodium alginate; (3) hydrogels set by exposure to either visible or ultraviolet light, e.g., polyethylene glycol polylactic acid copolymers with acrylate end groups; and (4) hydrogels that are set or solidified upon a change in pH, e.g., TETRONICS™.

Examples of materials that can be used to form these different hydrogels include polysaccharides such as alginate, polyphosphazenes, and polyacrylates, which are cross-linked ionically, or block copolymers such as PLURONICS™ (also known as POLOXAMERS™), which are poly(oxyethylene)-poly(oxypropylene) block polymers solidified by changes in temperature, or TETRONICS™ (also known as POLOXAMINES™), which are poly(oxyethylene)-poly(oxypropylene) block polymers of ethylene diamine solidified by changes in pH.

Ionic Hydrogels

Ionic polysaccharides, such as alginates or chitosan, can be used to suspend living cells. For this invention, the hydrogel is produced by cross-linking the anionic salt of alginic acid, a carbohydrate polymer isolated from seaweed, with ions, such as calcium cations. The strength of the hydrogel increases with either increasing concentrations of calcium ions or alginate. For example, U.S. Pat. No. 4,352,883 describes the ionic cross-linking of alginate with divalent cations, in water, at room temperature, to form a hydrogel matrix.

Tissue precursor cells are mixed with an alginate solution, the solution is applied to a tissue surface and then solidifies in a short time due to the presence in vivo of physiological concentrations of calcium ions.

In general, these polymers are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly (phosphazenes), poly(acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole).

Polyphosphazenes are polymers with backbones consisting of nitrogen and phosphorous atoms separated by alternating single and double bonds. Each phosphorous atom is covalently bonded to two side chains. Polyphosphazenes that can be used have a majority of side chains that are acidic and capable of forming salt bridges with di- or trivalent cations. Examples of acidic side chains are carboxylic acid groups and sulfonic acid groups.

Bioerodible polyphosphazenes have at least two differing types of side chains, acidic side groups capable of forming salt bridges with multivalent cations, and side groups that hydrolyze under in vivo conditions, e.g., imidazole groups, amino acid esters, glycerol, and glucosyl. Bioerodible or biodegradable polymers, i.e., polymers that dissolve or degrade within a period that is acceptable in the desired application (usually in vivo therapy), will degrade in less than about five years and most preferably in less than about one year, once exposed to a physiological solution of pH 6–8 having a temperature of between about 25° C. and 38° C. Hydrolysis of the side chain results in erosion of the polymer. Examples of hydrolyzing side chains are unsubstituted and substituted imidizoles and amino acid esters in which the side chain is bonded to the phosphorous atom through an amino linkage.

Methods for synthesis and the analysis of various types of polyphosphazenes are described in U.S. Pat. Nos. 4,440,921, 4,495,174, and 4,880,622. Methods for the synthesis of the other polymers described above are known to those skilled in the art. See, for example *Concise Encyclopedia of Polymer Science* and *Polymeric Amines and Ammonium Salts*, E. Goethals, editor (Pergamen Press, Elmsford, N.Y. 1980). Many polymers, such as poly(acrylic acid), alginates, and PLURONICS™, are commercially available.

Water soluble polymers with charged side groups are cross-linked by reacting the polymer with an aqueous solution containing multivalent ions of the opposite charge, either multivalent cations if the polymer has acidic side groups, or multivalent anions if the polymer has basic side groups. Cations for cross-linking the polymers with acidic side groups to form a hydrogel include divalent and trivalent cations such as copper, calcium, aluminum, magnesium, and strontium. Aqueous solutions of the salts of these cations are added to the polymers to form soft, highly swollen hydrogels and membranes.

Anions for cross-linking the polymers to form a hydrogel include divalent and trivalent anions such as low molecular weight dicarboxylate ions, terephthalate ions, sulfate ions, and carbonate ions. Aqueous solutions of the salts of these anions are added to the polymers to form soft, highly swollen hydrogels and membranes, as described with respect to cations.

Also, a variety of polycations can be used to complex and thereby stabilize the polymer hydrogel into a semipermeable surface membrane. Examples of one polycation is poly-L-lysine. There are also natural polycations such as the polysaccharide, chitosan.

For purposes of preventing the passage of antibodies across the membrane but allowing passage of nutrients essential for cellular growth and metabolism, a useful macromer/polymer size is in the range of between 10,000 D and 18,500 D. Smaller macromers result in polymer matrices of a higher density with smaller pores.

Temperature-Dependent Hydrogels

Temperature-dependent, or thermosensitive, hydrogels can be use in the methods of the invention. These hydrogels must have so-called "reverse gelation" properties, i.e., they are liquids at or below room temperature, and gel when warmed to higher temperatures, e.g., body temperature. Thus, these hydrogels can be easily applied at or below room temperature as a liquid and automatically form a semi-solid gel when warmed to body temperature. Examples of such temperature-dependent hydrogels are PLURONICS™ (BASF-Wyandotte), such as polyoxyethylene-polyoxypropylene F-108, F-68, and F-127, poly (N-isopropylacrylamide), and N-isopropylacrylamide copolymers.

These copolymers can be manipulated by standard techniques to affect their physical properties such as porosity, rate of degradation, transition temperature, and degree of rigidity. For example, the addition of low molecular weight saccharides in the presence and absence of salts affects the lower critical solution temperature (LCST) of typical thermosensitive polymers. In addition, when these gels are prepared at concentrations ranging between 5 and 25% (W/V) by dispersion at 4° C., the viscosity and the gel-sol transition temperature are affected, the gel-sol transition temperature being inversely related to the concentration. These gels have diffusion characteristics capable of allowing cells to survive and be nourished.

U.S. Pat. No. 4,188,373 describes using PLURONIC™ polyols in aqueous compositions to provide thermal gelling aqueous systems. U.S. Pat. Nos. 4,474,751, '752, '753, and 4,478,822 describe drug delivery systems which utilize thermosetting polyoxyalkylene gels; with these systems, both the gel transition temperature and/or the rigidity of the gel can be modified by adjustment of the pH and/or the ionic strength, as well as by the concentration of the polymer.

pH-Dependent Hydrogels

Other hydrogels suitable for use in the methods of the invention are pH-dependent. These hydrogels are liquids at, below, or above specific pH values, and gel when exposed to specific pHs, e.g., 7.35 to 7.45, the normal pH range of extracellular fluids within the human body. Thus, these hydrogels can be easily applied in the body as a liquid and automatically form a semi-solid gel when exposed to body pH. Examples of such pH-dependent hydrogels are TETRONICS™ (BASF-Wyandotte) polyoxyethylene-polyoxypropylene polymers of ethylene diamine, poly (diethyl aminoethyl methacrylate-g-ethylene glycol), and poly(2-hydroxymethyl methacrylate). These copolymers can be manipulated by standard techniques to affect their physical properties.

Light Solidified Hydrogels

Other hydrogels that can be used in the methods of the invention are solidified by either visible or ultraviolet light. These hydrogels are made of macromers including a water soluble region, a biodegradable region, and at least two polymerizable regions as described in U.S. Pat. No. 5,410,016. For example, the hydrogel can begin with a biodegradable, polymerizable macromer including a core, an extension on each end of the core, and an end cap on each extension. The core is a hydrophilic polymer, the extensions are biodegradable polymers, and the end caps are oligomers capable of cross-linking the macromers upon exposure to visible or ultraviolet light, e.g., long wavelength ultraviolet light.

Examples of such light solidified hydrogels can include polyethylene oxide block copolymers, polyethylene glycol polylactic acid copolymers with acrylate end groups, and 10K polyethylene glycol-glycolide copolymer capped by an acrylate at both ends. As with the PLURONIC™ hydrogels, the copolymers comprising these hydrogels can be manipulated by standard techniques to modify their physical properties such as rate of degradation, differences in crystallinity, and degree of rigidity.

Tissue Precursor Cells

Tissue precursor cells can be obtained directly from a mammalian donor, e.g., a patient's own cells, from a culture of cells from a donor, or from established cell culture lines. Preferably the mammal is a mouse, rat, rabbit, guinea pig, hamster, cow, pig, horse, goat, sheep, dog, cat, and most preferably, the mammal is a human. Cells of the same species and preferably of the same immunological profile can be obtained by biopsy, either from the patient or a close relative. Using standard cell culture techniques and conditions, the cells are then grown in culture until confluent and used when needed. The cells are preferably cultured only until a sufficient number of cells have been obtained for a particular application.

If cells are used that may elicit an immune reaction, such as human muscle cells from immunologically distinct donor, then the recipient can be immunosuppressed as needed, for example, using a schedule of steroids and other immunosuppressant drugs such as cyclosporine. However, the use of autologous cells will preclude such an immunologic reaction.

Cells can be obtained directly from a donor, washed, suspended in a selected hydrogel and applied (painted or sprayed) directly onto the surface in need of new tissue growth. To enhance cell growth, the cells are added or mixed with the hydrogel just prior to application.

Cells obtained by biopsy are harvested, cultured, and then passaged as necessary to remove contaminating, unwanted cells. The isolation of chondrocytes and osteoblasts is described in the example below.

The cells may be genetically altered or manipulated using standard techniques prior to suspending them in the hydrogel. For example, coronary endothelial cells can be genetically altered to secrete factors that inhibit thrombosis, or, chondrocytes can be genetically manipulated to respond to glucose challenge with the secretion of insulin.

Cell attachment and viability can be assessed using standard techniques including visual observation with a light or scanning electron microscope, histology, or quantitative assessment with radioisotopes. The biological function of the cells applied (painted or sprayed) onto the surface can be determined using a combination of the above techniques and standard functional assays.

Examples of cells that can be applied (painted or sprayed) onto a desired mammalian surface include epidermal cells; chondrocytes and other cells that form cartilage ("cartilage-forming cells"); macrophages; dermal cells; muscle cells; hair follicles; fibroblasts; organ cells; macrophages; osteoblasts and other cells that form bone ("bone forming cells"); endothelial cells; mucosal cells, e.g., nasal, gastric, bladder and oral mucosal cells; pleural cells; ear canal cells; tympanic membrane cells; peritoneal cells; Schwann cells; corneal epithelial cells; gingiva cells; and tracheal epithelial cells.

Preparation of Hydrogel-Cell Compositions

First, a hydrogel of choice is prepared using standard techniques. A biodegradable, thermosensitive polymer at a concentration ranging between 5 and 25% (W/V) is useful for the present invention. If the hydrogel is an alginate, it can be dissolved in an aqueous solution, for example, a 0.1 M potassium phosphate solution, at physiological pH, to a concentration between 0.5 to 2% by weight, e.g., 1%, to form an ionic hydrogel.

Second, isolated tissue precursor cells are suspended in the polymer solution at a concentration mimicking that of the tissue to be generated, e.g., between 10 and 100 million cells/ml, most preferably between 20 and 50 million cells/ml. The optimal concentration of cells to be applied onto a specific surface is determined on a case by case basis, and may vary depending on cellular type and surface. Optimization experiments require modifying only a few parameters, i.e., the cell concentration or the hydrogel concentration, to provide optimal viscosity and cell number to support the growth of new tissue.

For example, as demonstrated below, new growth of semi-transparent cartilaginous matrix, approximately 0.5 mm thick, was observed within two weeks after the application of a 0.5 mm thick layer of a hydrogel-cell composition containing approximately 50 million chondrocytes per ml.

Methods of Applying Hydrogel-Cell Compositions

The methods of the invention can be used for applying many different tissue precursor cell types onto many different surfaces to achieve tissue generation at the site of application. In one example, the tissue precursor cells are mixed with the hydrogel solution, preferably just prior to application, and then applied directly onto a surface where new tissue growth is desired. Within a short time after application, e.g., less than five minutes, and more preferably, less than 3 minutes, the hydrogel solidifies, thereby keeping the cells at the application site to optimize new cellular growth.

For example, the hydrogel-cell composition can be applied by painting directly onto a mammalian surface with several strokes of a sterile brush-like applicator or biopsy brush applicator. The bristles of such applicators must be sturdy enough to withstand sterilization, yet sufficiently supple not to damage the cells during the application (thereby reducing application traumatization), and must be soft and flexible enough to apply a thin, uniform layer of the hydrogel-cell composition onto the desired surface.

In another example, the hydrogel-cell composition can be aerosolized and sprayed directly onto a surface with a spraying device, e.g., shortly after the isolated cells are suspended in the desired hydrogel. Such devices are commonly employed in surgery to spray air or water over a desired surface. The spray pattern of the device must be gentle enough to not damage or shear the cells during the application and must be capable of providing a thin, uniform layer of hydrogel-cell composition onto the desired surface. For example, standard air brushes and manual spray pumps with nozzles can be used for this invention.

If the mammalian surface site is exposed by surgical resection, then the hydrogel-cell composition can be painted or sprayed directly onto the site. Alternatively, the surface can be viewed with the aid of, e.g., an endoscope, laparoscope, arthroscope, or esophagoscope, all of which can be modified to include a biopsy brush applicator, air brush, or other painting or spraying mechanism at the end of the device. When the desired application site is in view, the site is cleared of bodily fluids including blood, e.g., with a burst of air or suction, and the brush applicator or spraying device containing an aliquot of hydrogel-cell composition is used to apply the composition directly onto the site.

Thus, this hydrogel-cell composition can be introduced through a laparoscope, endoscope, laryngoscope, cystoscope, proctoscope, or thoracoscope to any the interior surface of any lumen or cavity, or other surfaces, such as intraperitoneal, extraperitoneal, and thoracic cavity, and then painted or sprayed onto the desired surface. For example, a thin layer of cells capable of new cell growth can be applied to ulcerated gastrointestinal regions to expedite the healing of ulcerated areas, or to the inside surface of injured blood vessels.

Care must be taken to cause minimal trauma to the cells during the application step. Cellular damage is avoided by using a proper brush applicator or spraying device. The amount of trauma caused during the application step can be determined by measuring a biological function specific for the cells being used. For example, when chondrocytes are being applied, the integrity of the new cartilage can be evaluated by standard biomechanical stress analyses.

To improve adhesion of the hydrogel-cell composition to a tissue surface, a biocompatible adhesive can be painted or sprayed onto the surface prior to application of the liquid hydrogel-cell composition. The adhesive can be a methyl alpha-cyanoacrylate, methacrylate, 2-cyano-2-propenoic acid methyl ester, methyl 2-cyanoacrylate, 2-cyanoacrylic acid methyl ester, or an n-butyl cyanoacrylate based glue. Suitable adhesive materials can also be incorporated into the hydrogel itself.

Thickness of Hydrogel-Cell Composition Layers

Once applied, the thickness of the hydrogel-cell composition should be the same as the thickness of the new tissue to be generated. The methods of application described above can be used to create a uniform hydrogel-cell composition layer of from tens of microns to between 0.5 and 5.0 mm in thickness.

For new cartilage formation, the thickness should be that of naturally occurring cartilage layers, e.g., preferably about 1.0 to 5.0 mm in humans, and somewhat narrower in smaller mammals. For newly generated skin, the hydrogel-cell composition layer could be a bi-laminate of a dermis cell layer and an epidermis cell layer, or an individual layer of only dermis cells or epidermis cells, depending on the specific situation. In each case, the layer would be approximately 0.5 to 5.0 mm thick. To produce a new epithelial cell lining within blood vessels, the layer should be 20 to 200 microns thick, depending on the type of blood vessel.

Layer thickness affects a variety of parameters, including perm-selectivity, rigidity, and thickness of the newly generated tissue. Thickness can be varied by modifying the parameters of the hydrogel, the cell concentration, and/or the method of application. For example, the hydrogel concentration can be varied depending on the polymer used. Similarly, for light solidified hydrogels (by either visible or ultraviolet light), more intense illuminations and longer illuminations will yield thicker layers than less intense or shorter illuminations. Accelerators can also be added in varying concentration to control thickness, e.g., N-vinyl pyrrolidone.

Ionic hydrogels form a somewhat thicker layer than other hydrogels since solidification occurs throughout the macromer solution. The thickness of the layers formed is determined in part by the viscosity of the macromer solution, the concentration of the macromer in that solution, the fluid mechanical environment of the suspension, and surface active agents in the suspension.

EXAMPLES

The present invention will be further understood by reference to the following non-limiting examples.

Example 1

Preparation of a Calcium-Alginate-Chondrocyte Composition

A calcium alginate mixture is obtained by combining calcium sulfate, a poorly soluble calcium salt, with a 1% sodium alginate dissolved in a 0.1 M potassium phosphate buffer solution (pH 7.4). The mixture remains in a liquid state at 4° C., and until its temperature is increased to over 15° C. Chondrocytes are isolated from cartilage tissue, e.g., the articular surface of calf forelimbs, using standard techniques, and are added to the mixture to generate a final cellular density of about 2 to $5\times10^7$/ml (e.g., representing approximately 10% of the cellular density of human juvenile articular cartilage).

Example 2

Preparation of a Thermosensitive Hydrogel-Chondrocyte Composition

A biocompatible, biodegradable, reverse-thermosensitive copolymer gel was obtained by preparing a 30% weight/volume solution of a PLURONIC™ F127 or F68 block copolymer (both available from BASF). The solution remains in a liquid state at less than 15° C., and solidifies within 5 to 10 minutes as the temperature is increased to over 15° C. Chondrocytes were isolated from the articular surface of calf forelimbs using standard techniques, and added to the hydrogel mixture to generate a final cellular density of about 2 to $6\times10^7$/ml.

Example 3

Application of a Thermosensitive Hydrogel-Chondrocyte Composition to Form Now Cartilage in Mice A biocompatible, biodegradable, reverse-thermosensitive copolymer hydrogel was obtained as described in Example 2. Cell concentration was selected to be about $5\times10^7$/ml.

The composition was then applied in mice in two selected sites, the connective tissue under the skin in the median dorsal region, which is an example of a soft tissue surface, and the bones of the cranium, from which the periosteum had been removed, which is an example of a hard tissue surface.

For the soft tissue application, an incision was made in the median dorsal region on each of ten athymic mice and an 0.1 ml aliquot of PLURONIC™ hydrogel-chondrocyte composition (approximately 50 million cell/ml) was applied to the exposed site using several strokes of a brush applicator to create a layer approximately 0.1 mm thick. The incision was sutured closed. Two mice were sacrificed at 2, 4, 6, 8, and 16 weeks after application, and the application sites were examined for cartilaginous matrix formation.

A semi-transparent cartilaginous matrix, approximately 0.1 mm thick, was observed as early as two weeks after the application. Histologic studies (specimens are stained with hematoxylin and eosin) confirmed the presence of cartilage. These results demonstrated that the PLURONIC™ copolymer hydrogel-chondrocyte composition can support new cartilage growth after being painted onto a soft tissue surface such as connective tissue.

For the hard tissue application, an incision was made in each of ten mice to expose the bones of their craniums, the periosteum was removed, and the bone surface was roughened using an osteotome. After the bleeding stopped, an 0.1 ml aliquot of PLURONIC™ hydrogel-chondrocyte composition (approximately 50 million cells/ml) was applied to the exposed site using several strokes of a brush applicator to create a layer approximately 0.5 mm thick. The incision was sutured closed. Two mice were sacrificed at 2, 4, 6, 8, and 16 weeks after surgery and the application site was examined for cartilaginous matrix formation. This same example can be conducted using osteoblasts to evaluate formation of new bone tissue.

As in the soft tissue example, a semi-transparent cartilaginous matrix, this time approximately 0.5 mm thick, was observed as early as two weeks after the application. Histologic studies confirmed the presence of cartilage. These results demonstrated that PLURONIC™ copolymer hydrogel-chondrocyte compositions can support new cartilage growth after being painted onto a hard, bony surface.

In another example, a PLURONIC™ hydrogel was seeded with bovine chondrocytes obtained from articular hyaline cartilage at a concentration of 50 million cells/ml as described above. The hydrogel-chondrocyte composition was painted as a liquid onto the surface of porous coral (hydroxyapatite) disks approximately ½ inch in diameter and 7 to 8 mm thick. Hydroxyapatite is the primary structural element of vertebrate bone and thus serves as a good model for bone. These disks were then implanted subcutaneously on the dorsum of nude (athymic) mice for period of 4 to 6 weeks.

Eight disks were excised at the end of the time period and evaluated using both gross and histological techniques, as described above. The surface of each of the excised disks was covered with a uniform layer of cartilage about 2 to 3 mm thick and extending an additional 1 to 2 mm into the surface of the porous hydroxyapatite. The cartilage that penetrated the disk surface was well incorporated and adhered very well to the surface of the hydroxyapatite.

All of these examples in the mouse model provide evidence that the same techniques, using the same hydrogels with human chondrocytes, will be effective to generate a new surface layer of cartilage in human patients. In each of these examples, the thermo-sensitive hydrogel behaved in the same way. As the temperature of the hydrogel-cell composition approached body temperature, the liquid hydrogel-cell composition solidified, thereby causing the chondrocytes to adhere to the application site surface. As the hydrogel degraded, a thin layer of newly formed cartilage remained at the application site.

Example 4

Application of a Calcium Alginate-Chondrocyte Composition to Form New Cartilage in Mice A calcium alginate composition is obtained as described in Example 1. Cell concentration is selected to be 50 million cells/ml.

Approximately 0.1 to 0.5 mls of the calcium alginate-chondrocyte composition is applied to the desired surface in nude mice by painting with several brush strokes of a brush-like applicator. Identical surfaces of control mice are painted with calcium alginate only (without chondrocytes) and are analyzed in the same manner as the experimental group of mice. The calcium alginate-chondrocyte composition is applied in a uniform layer of cells between about 200 and 500 microns in thickness.

The mice are harvested 2, 4, 6, 8, and 12 weeks after application, and are analyzed for cartilage formation at the site of application. The calcium alginate-chondrocyte specimens are examined by gross and histological examination, as described above. Histologically, the specimens are stained with hematoxylin and eosin and analyzed.

Example 5

Application of a Thermosensitive Hydrogel-Chondrocyte Composition to Form New Cartilage in Rabbit Knees The efficacy of the system was evaluated in immune competent animals using autologous articular chondrocytes from the knee of New Zealand white rabbits. In this example, a biopsy of articular cartilage was first taken from the patella groove in the distal femur of New Zealand white rabbits. Chondrocytes were isolated from these biopsied specimens by a series of enzymatic digestions and then allowed to multiply in vitro at 37° C. in 5% $CO_2$ in a media composed of Hamm's F12 and 10% fetal bovine serum. After a sufficient number of cells were obtained, the contralateral knee of the same New Zealand white rabbit from which the cells had been obtained was exposed, and a ⅜ inch diameter defect approximately ⅜ to ½ inch in depth was created perpendicular to the surface of the joint extending into the femoral bone.

The defect then was primarily filled with a coral (hydroxyapatite) dowel machined to be ⅜ inch in diameter and ⅜ inch in depth. After the dowel was placed into the defect, the surface of the dowel was shaped by use of a Dremel drill to reproduce the surface contour of the distal femur. The coral dowel was then countersunk to a depth of 1 mm below the original surface of the knee.

A reverse-thermosensitive copolymer hydrogel was obtained as described in Example 2 and seeded with between 10 and 50 million cells per ml using the autologous articular cartilage chondrocyte cells. The surface of the defect which had been repaired with the coral dowel was then painted with the hydrogel-cell composition and the knee surgically closed. After four weeks of implantation, the rabbits were sacrificed and the distal femur was studied using both gross and using histological techniques, as described above.

A total of four rabbits were studied, and in each case, a large percentage of the surface area of the implanted coral dowels was covered with what appeared to be a glistening, white hyaline cartilage, approximately 2 to 4 mm thick and extending another 1 to 2 mm into the surface of the coral (hydroxyapatite) dowel, where it was well incorporated. In addition, bone cells from the joint were well incorporated and filled into the coral plugs below the level of cartilage penetration. In two of the four rabbits, an inflammatory reaction was noted at the four week analysis.

This example in the rabbit model provides evidence that the same techniques, using the same hydrogels with human chondrocytes, will be effective to replace an entire joint, while repairing the surface with "cartilage paint," in human patients.

Example 6

Effect of Cell Density on Cartilage Formation

The assay in this Example is used to determine the optimal concentration of chondrocytes capable of supporting new chondrocyte growth as well as subsequent cartilage formation.

Varying numbers of chondrocytes isolated from the articular surface of calf forelimbs are mixed with either a 1.5% sodium alginate solution or a biocompatible, biodegradable, reverse-thermosensitive copolymer gel (PLURONIC™; 30% (w/v) copolymer gel) to generate final cell densities of 0.0, 0.5, 1.0, 2.0, and $5.0 \times 10^7$ chondrocytes/ml. Different numbers of cells are applied to the desired nude mouse surface, e.g., the bones of the cranium as described above, in a 0.1 ml aliquot of hydrogel-cell solution. Samples are harvested at 2, 4, 6, 8, and 12 weeks and examined for gross and histological evidence of optimal cartilage formation. Similar experiments can be done to determine optimal hydrogel viscosity and concentration, as well as thickness of the painted hydrogel-cell composition layer.

Example 7

Preparation of Hydrogel-Epithelial Cell Compositions and Application to Blood Vessel Lumens This method is useful to form layers of new endothelial or epithelial cells in a tissue lumen such as a blood vessel, or for repairing lesions or replacing damaged cells on the inside of blood vessels due to angioplasty or other vessel injury. Autologous endothelial cells are obtained, washed, and mixed with a hydrogel, e.g., a thermosensitive hydrogel.

In the dog model, carotid arteries are exposed surgically and clamped to isolate about 2 to 3 cm regions. The vessels are artificially injured by crushing with a hemostat. The isolated zones are cleaned and rinsed with a syringe containing sterile saline.

Approximately 0.1 to 0.5 mls of the hydrogel-endothelial cell composition is applied to the lining of the carotid arteries by painting with several brush strokes of a biopsy brush attachment of an endoscope. Identical surfaces in control animals are painted with hydrogel only (without cells) and are analyzed in the same manner as the treated group, e.g., using gross and histological techniques, as described above.

Optimal cell concentrations may vary from mammal to mammal, but should be between 10 and 60 million cells/ml, e.g., between 20 and 50 million cells/ml. The hydrogel-endothelial cell composition should be applied to create a uniform layer between 10 and 500 microns in thickness, e.g., about 20 to 50 microns in thickness, depending on the type of blood vessel.

After 5 minutes, the clamps are removed to allow normal blood flow. The application site is histologically examined two, four, six, and eight weeks after application to determine the amount of new cell lining growth at the application sites. Success in the dog model provides evidence that the same techniques, using human endothelial cells, will be effective to generate new endothelial tissue within blood vessels in human patients.

Example 8

Preparation of Hydrogel-Epidermal Cell Composition and Application to Skin

The methods of the invention are also useful to generate new skin tissue to replace lost skin, e.g., due to wounds and burns. Autologous epidermal and/or dermal cells are obtained, washed, and mixed with a desired hydrogel.

In the mouse model, athymic mice dorsal skin is abraded to create a wound either through the epidermal cell layer only or through both the epidermal and dermal cell layers. For wounds only to the epidermal cell layer, approximately 0.1 to 0.5 mls of the hydrogel-epidermal cell composition is applied to the skin by painting with several brush strokes or by spraying directly onto the area after the bleeding has stopped.

If the abrasion wounded both the epidermal and dermal cell layers, either (1) a thin layer of hydrogel-dermal cell composition is applied to the wound as described above and allowed to solidify before applying a thin layer of the hydrogel-epidermal cell composition, or (2) a thin layer of hydrogel-dermal cell composition is applied to the wound as described above and allowed to solidify and become vascularized before applying a thin layer of a hydrogel-epidermal cell composition.

Optimal cell concentration may vary from mammal to mammal, but should be between 10 and 60 million cells/ml, e.g., between 20 and 50 million cells/ml. The hydrogel-epidermal cell composition and hydrogel-dermal cell composition are applied to create two layers between 0.2 and 2.0 mm in thickness, e.g., to match the thickness of normal skin at the site.

The application site is histologically examined two, four, six, and eight weeks after application to determine the amount of new skin growth at the application sites. Success in the mouse model provides evidence that the same techniques, using human dermal and epidermal cells, will be effective to generate new skin tissue in human patients.

Example 9

Preparation of Hydrogel-Stomach Epithelial Cell Composition and Application to Correct Ulcerated Stomach Lesions The methods of the invention are also useful in correcting ulcerated lesions in the gastrointestinal lining. Autologous stomach epithelial cells are obtained, washed, and mixed with a desired hydrogel, e.g., a thermosensitive or light solidified hydrogel.

In the dog model, dog stomach linings are abraded to create a lesion about 0.5 mm to 1.0 mm deep. When the bleeding stops, approximately 0.1 to 0.5 mls of the hydrogel-epithelial cell composition is applied to the stomach lining by painting with several brush strokes of a biopsy brush attachment for an endoscope. The hydrogel solidifies, e.g., upon exposure to the body temperature of the dog, or by exposure to light of the appropriate wavelength.

Optimal cell concentration may vary from mammal to mammal, but should be between 10 and 60 million cells/ml, and most preferably between 20 and 50 million cells/ml. The hydrogel-epithelial cell composition is applied to create a uniform layer between 0.5 and 3.0 mm in thickness, e.g., to match the thickness of normal stomach lining.

The application site is histologically examined two, four, six, and eight weeks after application to determine the amount of new stomach lining growth at the application sites. Success in the dog model provides evidence that the same techniques, using human epithelial cells, will be effective to generate new stomach lining tissue in human patients.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

I claim:

1. A method for generataing new living tissue on and external surface of a tissue structure or organ in a mammal, said method comprising:
   a) obtaining a liquid hydrogel-cell composition comprising a hydrogel and live tissue precursor cells;
   b) applying a thin layer of said liquid hydrogel-cell composition to the external surface in the mammal; and
   c) allowing said applied liquid hydrogel-cell composition to solidify, thereby forming a matrix that enables the tissue precursor cells to grow and generate new living tissue.

2. A method of claim 1, wherein said hydrogel-cell composition is solidified upon exposure to the body temperature of the mammal.

3. A method of claim 1, wherein said hydrogel-cell composition is solidified by interaction with ions selected from the group consisting of copper, calcium, aluminum, magnesium, strontium, barium, tin, and di-, tri- or tetra-functional organic cations, low molecular weight dicarboxylate ions, sulfate ions, and carbonate ions.

4. A method of claim 1, wherein said hydrogel-cell composition is solidified upon exposure to radiation.

5. A method of claim 1, wherein the hydrogel is selected from the group consisting of polysaccharides, proteins, polyphosphazenes, poly(oxyethylene)-poly(oxypropylene) block polymers, poly(oxyethylene)-poly(oxypropylene) block polymers of ethylene diamine, poly(acrylic acids), poly(methacrylic acids), copolymers of acrylic acid and methacrylic acid, poly(vinyl acetate), and sulfonated polymers.

6. A method of claim 1, wherein said hydrogel-cell composition is further stabilized by cross-linking with a polyion.

7. A method of claim 1, wherein the tissue precursor cells are selected from the group consisting of epidermal cells, chondrocytes and other cells that form cartilage, macrophages, dermal cells, muscle cells, hair follicles, fibroblasts, organ cells, osteoblasts and other cells that form bone, endothelial cells, mucosal cells, pleural cells, ear canal cells, tympanic membrane cells, peritoneal cells, Schwann cells, corneal epithelial cells, gingiva cells, and tracheal epithelial cells.

8. A method of claim 1, wherein said liquid hydrogel-cell composition is applied by painting, spraying, or dripping said composition onto the surface.

9. A method of claim 1, wherein said method further includes the use of a biocompatible amount of an adhesive selected from the group consisting of methyl alpha-cyanoacrylate, methacrylate, 2-cyano-2-propenoic acid methyl ester, methyl 2-cyanoacrylate, 2-cyanoacrylic acid methyl ester, and n-butyl cyanoacrylate based glue.

10. A method of claim 1, wherein said mammal is a human, mouse, rat, rabbit, cow, pig, horse, goat, sheep, dog, or cat.

11. The method of claim 1, wherein the applied thin layer has a thickness of from about tens of microns to between 0.5 and 5.0 mm.

12. The method of claim 1, wherein the matrix degrades as the new tissue grows.

13. A method for generating new living skin on an external surface of damaged skin on a mammal, said method comprising:
   a) obtaining a liquid hydrogel-cell composition comprising a hydrogel and skin precursor cells;
   b) applying a thin layer of said liquid hydrogel-cell composition to the external surface of damaged skin on the mammal; and
   c) allowing said applied liquid hydrogel-cell composition to solidify, thereby forming a matrix that enables the skin precursor cells to grow and generate new living skin.

14. A method of claim 13, wherein said hydrogel-cell composition is applied in two layers, with a first hydrogel-cell layer comprising dermal cells and a second hydrogel-cell layer comprising epidermal cells.

15. A method for generating new living cartilage on an external surface of damaged cartilage in a mammal, said method comprising:
   a) obtaining a liquid hydrogel-cell composition comprising a hydrogel and live chondrocytes;
   b) applying a thin layer of said liquid hydrogel-cell composition to the external surface of the damaged cartilage in the mammal; and
   c) allowing said applied liquid hydrogel-cell composition to solidify, thereby forming a matrix that enables the chondrocytes to grow and generate new living cartilage.

16. The method of claim 15, wherein said hydrogel is a temperature-sensitive hydrogel, and said liquid hydrogel-cell composition is solidified upon exposure to the body temperature of said mammal.

17. The method of claim 15, wherein said liquid hydrogel-cell composition is applied to said damaged cartilage surface by painting, spraying, or dripping said composition onto the surface.

* * * * *